United States Patent [19]

Skurikhin et al.

[11] 4,187,541

[45] Feb. 5, 1980

[54] DIGITAL ANALYZER FOR DETERMINING LIQUIDUS TEMPERATURE OF METALS AND ALLOYS

[75] Inventors: Vladimir I. Skurikhin; Leonid S. Fainzilberg; Leonid S. Zhitetsky, all of Kiev, U.S.S.R.

[73] Assignee: Institut Kibernetiki Akademii Nauk Ukrainskoi SSR, Kiev, U.S.S.R.

[21] Appl. No.: 913,910

[22] Filed: Jun. 8, 1978

[30] Foreign Application Priority Data

Jun. 13, 1977 [SU] U.S.S.R. ............................... 2496567

[51] Int. Cl.² ...................... G06F 15/20; G01N 25/02
[52] U.S. Cl. .................................. 364/497; 73/17 R; 75/130 R; 266/80; 364/472; 364/557
[58] Field of Search ............... 364/472, 477, 496, 497, 364/499, 500, 557; 75/59, 60, 130 R, 132, 133, 129; 73/17 R, 341, 359, 360, 361, DIG. 9; 324/103 R, 103 P, 104; 266/80

[56] References Cited

U.S. PATENT DOCUMENTS

| | | | |
|---|---|---|---|
| 3,329,495 | 7/1967 | Ohta et al. | 364/497 X |
| 3,475,599 | 10/1969 | Schwartzenberg et al. | 364/500 X |
| 3,816,720 | 6/1974 | Bauer et al. | 364/500 |
| 3,819,834 | 6/1975 | Warsinski | 364/497 |
| 3,824,837 | 7/1975 | Nagaoka et al. | 73/17 R |
| 4,088,974 | 5/1978 | Zhitetsky et al. | 364/499 X |

*Primary Examiner*—Joseph F. Ruggiero
*Attorney, Agent, or Firm*—Haseltine, Lake & Waters

[57] ABSTRACT

A digital analyzer for determining the liquidus temperature of metals and alloys comprising a converter of the actual temperature of metals and alloys to a digital pulse code which is connected via a synchronization unit to a reversible counter and to a discriminator of local temperature increments. Outputs of the converter are connected to reset inputs of a first time interval discriminator and to reset inputs of a second time interval discriminator. Count inputs of the first and second time interval discriminators are connected via the synchronization unit to a clock pulse generator. An intermediate output of the first time interval discriminator is connected to a disable input of the second time interval discriminator having an intermediate output connected to a control input of a register, an output of the first time interval discriminator and that of the second time interval discriminator being connected via an OR gate to a control input of a digital display unit which is connected via the register to the reversible counter.

2 Claims, No Drawings

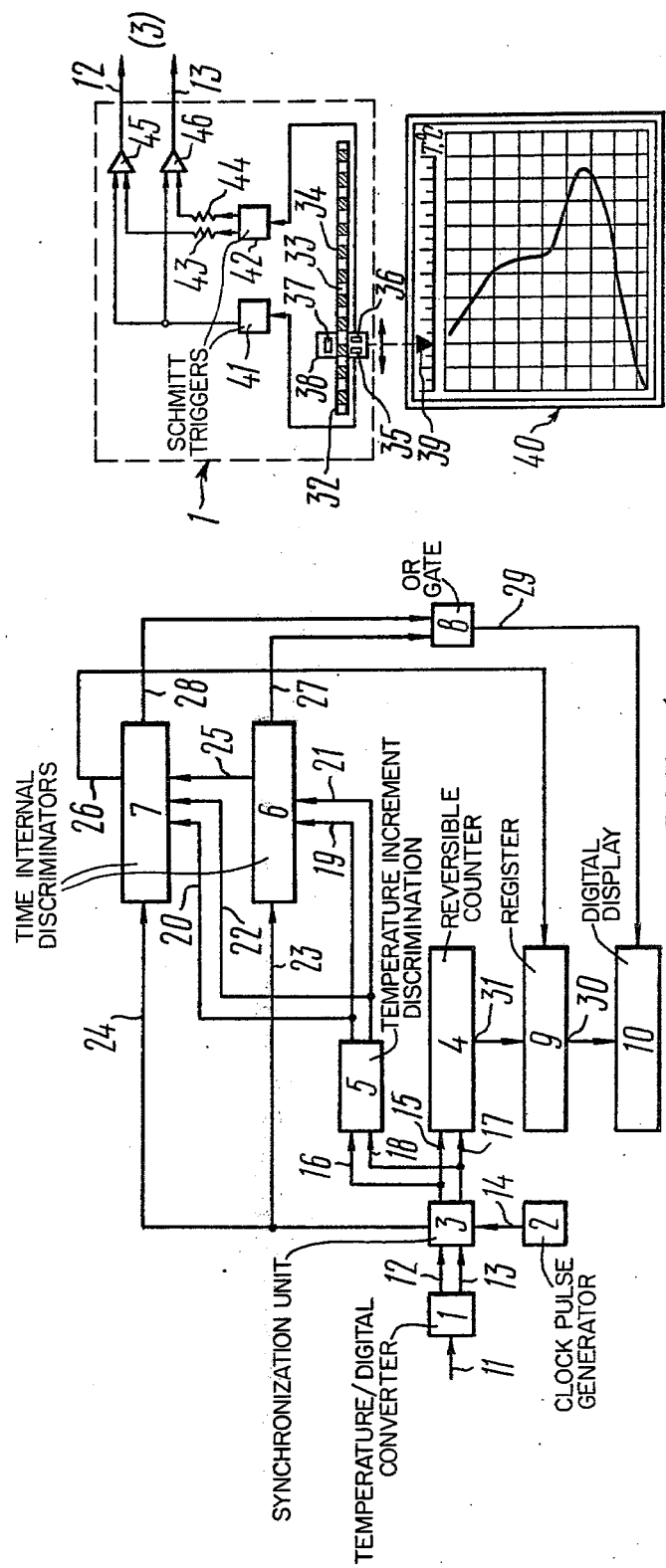

DIGITAL ANALYZER FOR DETERMINING LIQUIDUS TEMPERATURE OF METALS AND ALLOYS

FIELD OF THE INVENTION

The present invention relates to digital measuring devices for checking parameters of molten metals and alloys and, in particular, to digital analyzers for determining the liquidus temperature of metals and alloys.

The invention can be employed in automatic systems for checking and controlling steel melting processes.

DESCRIPTION OF THE PRIOR ART

Known in the art is a digital device for automatic checking of the carbon content in metal with reference to thermal arrests of the cooling curve (cf. UK Pat. No. 1,477,564), comprising a converter for converting the actual temperature of metals and alloys to a digital pulse code, to whose input there is applied a signal carrying information on the actual temperature of metals and alloys in the process of their cooling, whereas at its outputs there are formed code pulses corresponding to positive and negative temperature increments. The device also includes a clock pulse generator. Through a synchronization unit for distributing code and clock pulses in time, outputs of said converter are connected to add and subtract inputs of a reversible counter, and to inputs of a discriminator of local temperature increments. The reversible counter produces a parallel actual temperature code. The discriminator of local temperature increments is adjusted so that at one of its outputs there is formed a pulse whenever a certain positive or negative value $\epsilon_0$ is set therein. The output of the generator is coupled via the synchronization unit to a count input of a time interval discriminator intended for selecting time intervals during which predetermined temperature increments $\pm\epsilon_0$ occur. Reset inputs of the time interval discriminator are connected to outputs of the discriminator of local temperature. The time interval discriminator is designed so that at its output there is formed a signal only if the selected time interval exceeds a predetermined threshold $\tau_0$. An output of the time interval discriminator is connected to a control input of a register which, in turn, is connected with its information input to an information output of the reversible counter, and with its information output to an information input of a digital display unit. A control unit of the digital display unit is connected to an output of an OR gate to one of whose inputs a signal is applied at a moment when a decision is made to terminate the analysis.

The above device operates as follows. Code pulses from the converter for converting the actual temperature of metals and alloys to a digital pulse code are fed through the synchronization unit to the inputs of the discriminator of local temperature increments and to the add and subtract inputs of the reversible counter which in response generates a parallel code of the actual temperature. Each time the temperature increment is equal to $\pm\epsilon_0$, at a respective output of the discriminator of local temperature increments there is formed a pulse which is applied to the reset inputs of the time interval discriminator.

The count input of the time interval discriminator is fed with synchronized clock pulses. After each resetting, the time interval discriminator again starts counting synchronized clock pulses. At the end of a predetermined time interval $\tau_0$ after the last resetting of the time interval discriminator, there appears a pulse at the output thereof, which occurs only if the next pulse does not arrive at the reset inputs of the time interval discriminator within the time interval $\tau_0$. From the output of the latter, the pulse is applied to the control input of the register. The content of the reversible counter is entered into the register. As soon as the signal is applied from the output of the OR gate to the digital display unit, the latter produces a digital display of the result of the analysis.

Thus the device under review automatically determines the liquidus temperature only when on the cooling curve there occur such anomalous horizontal or sloping portions, whereat the metal temperature change during the time equal to $\tau_0$ does not exceed the value $\pm\tau_0$.

When an anomalous sloping portion occurs on the cooling curve, the liquidus temperature is determined by the temperature at the break point of the cooling curve, i.e. at the starting point of the anomalous portion. In this case, as follows from the foregoing description of the device, the result of analysis, entered into the register may differ from the liquidus temperature by $\epsilon_0$. Therefore the $\epsilon_0$ threshold is set with due regard for accuracy requirements determining of the liquidus temperature.

In practice, on the cooling curves there also may be such anomalous sloping portions caused by the thermal effect of phase transformation of metals and alloys, whereat the temperature change during the time $\epsilon_0$ exceeds the $\epsilon_0$ threshold.

As pointed out above, an increase in the $\epsilon_0$ threshold is impermissible because it leads to a greater error in determining the liquidus temperature. Decreasing the $\epsilon_0$ threshold for the purpose of detection of the anomalous sloping portion having a steep droop is also impermissble in so far as in this case there may be detected an anomalous sloping portion of a short duration, caused by the pseudothermic effect, whereat the metal temperature at the break point of the cooling curve may be mistaken for the liquidus temperature.

Thus the known device does not provide for a sufficient confidence of detecting anomalous sloping portions caused by the thermal effect of phase transformation of metals and alloys.

SUMMARY OF THE INVENTION

It is an object of the present invention to provide a digital analyzer for determining liquidus temperature of metals and alloys which eliminates the above disadvantages and improves the accuracy of detecting an anomalous sloping portion due to the thermal effect of phase transformation. The invention essentially aims at providing, on the basis of simple elements and units of digital computing equipment, a digital analyzer for determining the liquidus temperature of metals and alloys, wherein by storing the temperature corresponding to breaks of the cooling curve and subsequent checking of the duration anomalous portion during the analysis process there is obtained a higher accuracy of detecting the anomalous sloping portion caused by the thermal effect of phase transformation of metals and alloys.

These and other objects are attained by the digital analyzer of the invention.

BRIEF DESCRIPTION OF THE SEVERAL VIEWS OF THE ACCOMPANYING DRAWINGS

These and other objects and advantages of the present invention will become more apparent from the following detailed description of a preferred embodiment thereof, taken in conjunction with the accompanying drawings, wherein:

FIG. 1 is a block diagram of a digital analyzer for determining the liquidus temperature of metals and alloys according to the invention;

FIG. 2 is a functional diagram of a converter for converting the actual temperature of metals and alloys to a digital pulse code according to the invention;

Figure 9:
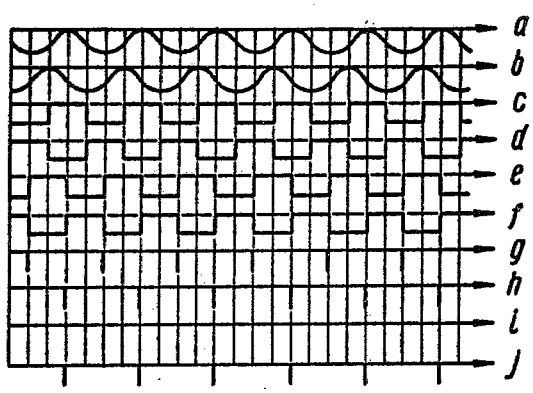
Figure 10:
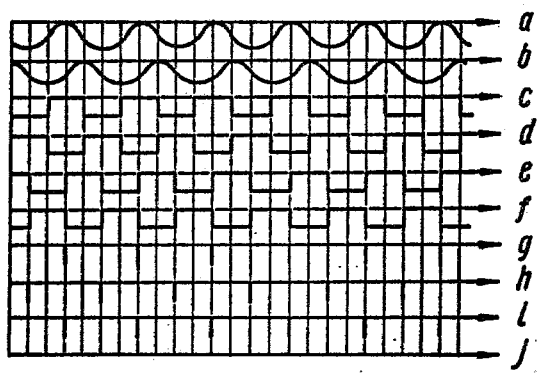
Figure 11:
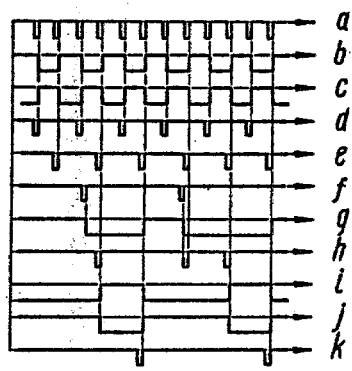

FIGS. 9 a, b, c, d, e, f, g, h, i, j are time plots illustrating operation of the converter for converting the actual temperature of metals and alloys to a digital pulse code with a positive increment in the temperature on the cooling curve;

FIGS. 10 a, b, c, d, e, f, g, h, i, j are time plots of FIG. 9, but with a negative increment in the temperature on the cooling curve;

FIGS. 11 a, b, c, d, e, f, g, h, i, j, k, are time plots illustrating operation of the synchronization unit.

DETAILED DESCRIPTION OF THE INVENTION

The proposed digital analyzer for determining the liquidus temperature of metals and alloys can be employed in combination with any known measuring device that can produce a cooling curve.

The digital analyzer for determining the liquidus temperature of metals and alloys is shown in FIG. 1 and comprises a converter 1 for converting the actual temperature of a metal or alloy to a digital, pulse code, a clock pulse generator 2, a synchronization unit 3 for distributing in time code and clock pulses a reversible counter 4 for generating a parallel code of temperature, a local temperature increments discriminator 5, a first time interval discriminator 6 for selecting time intervals during which a predetermined increment of temperature occurs, a second time interval discriminator 7 for selecting time intervals during which a predetermined increment of temperature occurs within a period of time exceeding the predetermined value, an OR gate 8, a register 9 for storing the of the results analysis, and a digital display unit 10 for displaying the results of the analysis in a digital form.

The converter 1 has an input 11 whereto there is applied signal carrying information on the actual temperature of a metal or alloy in the process of their cooling, an output 12 for code pulses corresponding to a positive temperature increment, and an output 13 for code pulses corresponding to a negative temperature increment. The outputs 12 and 13 are connected to inputs of the synchronization unit 3.

An output 14 of the clock pulse generator 2 is connected to a third input of the synchronization unit 3. The output of the synchronization unit 3, for synchronized code pulses corresponding to a positive increment in temperature, is connected to an add input 15 of the reversible counter 4 and to an input 16 of the discriminator 5. Another output of the synchronization unit 3, for code pulses corresponding to a negative increment in temperature, is connected to a subtract input 17 of the reversible counter 4 and to inputs 18 of the discriminator 5. A first output of the discriminator 5, for delivering a signal in case of a predetermined positive increment of temperature, is connected to a first reset input 9 of the discriminator 6 and to a first input 20 of the discriminator 7. A second output of the discriminator 5, for delivering a signal in case of a predetermined negative increment of temperature, is connected to a second reset input 21 of the discriminator 6 and to a second reset input 22 of the discriminator 7.

A count input 23 of the discriminator 6 and a count input 24 of the discriminator 7 are connected to a third output of the synchronization unit 3, for delivering synchronized clock pulses.

An intermediate output 25 of the discriminator 6 is connected to a disable input of the discriminator 7 whereas an intermediate output 26 of the discriminator 7 is connected to a control input of the register 9. An output 27 of the discriminator 6 and an output 28 of the discriminator 7 are connected to inputs of the OR gate 8 whose output 29 is connected to a control input of the digital display unit 10.

An information input of the digital display unit 10 is connected to an information output 30 of the register 9 having an information input connected to an information output 31 of the reversible counter 4.

The discriminator 5 of the local temperature increments is adjusted so that at its first output there is formed a pulse at the moment when a positive local increment of temperature assumes the predetermined value $+\epsilon_0$, whereas at its second output there is formed a pulse at the moment when a negative local temperature increment assumes a predetermined value $-\epsilon_0$.

The discriminator 5 of local temperature increments may be constructed as a reversible counter whose add and subtract inputs are the inputs of the discriminator 5, whereto there are fed synchronized code pulses corresponding to positive and negative increments of temperature. An add overflow output of the counter serves as a first output of the discriminator 5 whereat there is formed a digital in case of a predetermined positive increment of temperature. A subtract overflow output of the counter is a second output of the discriminator 5, whereat there is formed a signal in case of a predetermined negative increment of temperature. Other versions of the discriminator of local temperature increments are also possible.

The discriminator 6 is adjusted so that after each resetting at the intermediate output 25 after a certain time equal to $\tau_{01}$ there is formed a pulse, if during this time the discriminator 6 is not reset again, whereas at its output 27 after a certain time $\tau_{02}$ there is formed a signal if during this time the discriminator 6 is not reset again, the value $\tau_{02}$ being greater than the values $\tau_{01}$.

The discriminator 7 is adjusted so that after each resetting, at the intermediate output 26 after a certain time there is formed a pulse if during this time the discriminator 7 is not reset again, whereas at its output 28 after a time $\tau_{03}$ there is formed a signal if during this time the discriminator 7 is not reset again, the value $\tau_{03}$ being greater than the value $\tau_{02}$. FIG. 2 illustrates an alternative embodiment of the converter 1 for converting the actual temperature of metals and alloys to a digital pulse code, to whose input there is applied a signal carrying information on the temperature of a metal or alloy being cooled. In this case the input 11 of the converter 1 may be mechanically coupled, for example, to a slide contact of an automatic potentiometer whereto a signal is continuously fed from a temperature sensor.

The converter 1 comprises a measuring scale 32 whereon there are alternate transparent marks 33 and non-transparent marks 34 of an equal width. The number of the marks determines the resolving power of the converter 1. The converter 1 further comprises two photodiodes 35, 36 and a light source 37 which are mountef on a holder 38. The photodiodes 35, 36 are spaced at a distance equal to half the width of the marks 33, 34.

The holder 38 of the converter 1 is mechanically coupled to a slide contact 39 of the automatic potentiometer 40.

In addition, the converter 1 includes two Schmitt triggers 41, 42, two pulse shapers 43, 44 at a positive edge of signals arriving from outputs of the Schmitt trigger 42, and two gates 45, 46 for selecting code pulses corresponding to positive and negative temperature increments on the cooling curve.

The input of the Schmitt trigger 41 is connected to the output of the photodiode 35, whereas the input of the Schmitt trigger 42 is connected to the output of the photodiode 36. The reset output of the Schmitt trigger 41 is connected to the control inputs of the gates 45 and 46.

The set output of Schmitt trigger 42 is connected to the input of the pulse shaper 43, whereas the reset output of the Schmitt trigger 42 is connected to the input of the pulse shaper 44.

The output of the pulse shaper 43 is connected to the pulse input of the gate 45, whereas the output of the pulse shaper 44 is connected to the pulse input of the gate 46.

At the outputs of the gates 45, 46 there are formed code pulses of the converter 1, corresponding to positive and negative temperature increments on the cooling curve.

Figure 3:
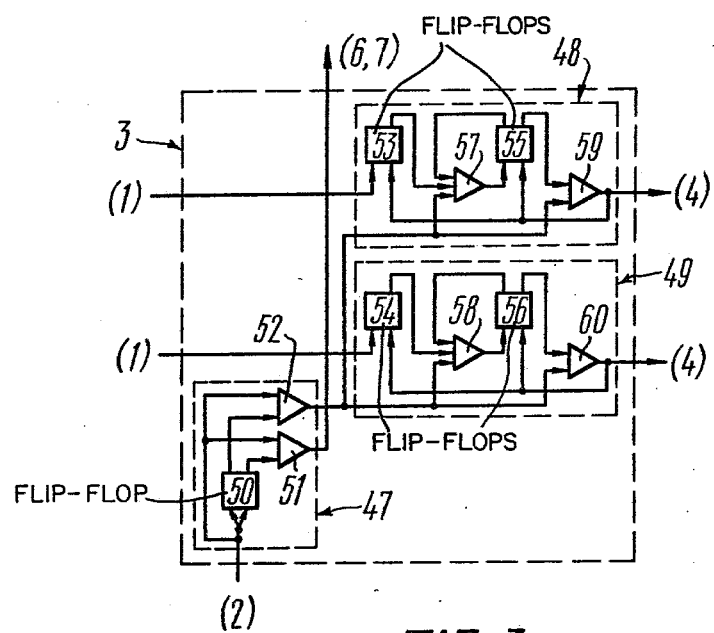
FIG. 3 is a functional diagram of a synchronization unit in according with the invention.

There may be other versions of the converter of the actual temperature of metal to a digital pulse code. FIG. 3 illustrates an alternative embodiment of the synchronization unit of code and clock pulses. The synchronization unit 3 includes a unit 47 for distributing clock pulses, as well as units 48 and 49 for synchronizing code pulses. The clock pulse distribution unit 47 comprises a flip-flop 50 for distributing clock pulses, a gate 51 for forming synchronized clock pulses, and a gate 52 for forming synchronizing clock pulses. Control inputs of the gates 51 and 52 are connected to outputs of the flip-flop 50. Pulse inputs of the gates 51 and 52 are combined and connected to the count input of the flip-flop 50, and serve as a third input of the synchronization unit 3 whereto there are fed pulses from the clock pulse generator 2. The output of the gate 51 is the third output of the synchronization unit 3. The code pulse synchronization units 48 and 49 comprise flip-flops 53 and 54 for storing code pulses, buffer flip-flops 55 and 56, AND gates 57 and 58, and gates 59 and 60 for forming synchronized code pulses. The set input of the flip-flop 53 is the input of the synchronization unit 3 whereto there are fed code pulses corresponding to a positive increment of temperature on the cooling curve. The set input of the flip-flop 54 is the input of the synchronization unit 3 whereto there are fed code pulses corresponding to a negative increment of temperature on the cooling curve. Inputs of the AND gate 57 are connected to the set output of the flip-flop 53 and to the reset output of the flip-flop 55.

Inputs of the AND gate 58 are connected to the set output of the flip-flop 54 and to the reset output of the flip-flop 56. The third input of each of the AND gates 57 and 58 is connected to the output of the gate 52 for forming synchronizing clock pulses of the distributing unit 47. The output of the gate 52 is also connected to one input of the gate 59 of the synchronization unit 48 and to one input of the gate 60 of the synchronization unit 49. The other inputs of each of the gates 59 and 60 are connected to set outputs of the flip-flops 55 and 56. The output of the AND gate 57 is connected to the set input of the flip-flop 55, whereas the output of the AND gate 58 is connected to the set input of the flip-flop 56. The output of the gate 59 is connected to reset inputs of the flip-flops 53 and 55 and is the output for synchronized code pulses of the synchronization unit 3, whereto there are applied code pulses corresponding to a positive increment of temperature on the cooling curve. The output of the gate 60 is connected to reset inputs of the flip-flops 55 and 56 and serves as the output for synchronized code pulses of the synchronization unit, whereto there are applied code pulses corresponding to a negative increment of temperature on the cooling curve.

Figure 4:
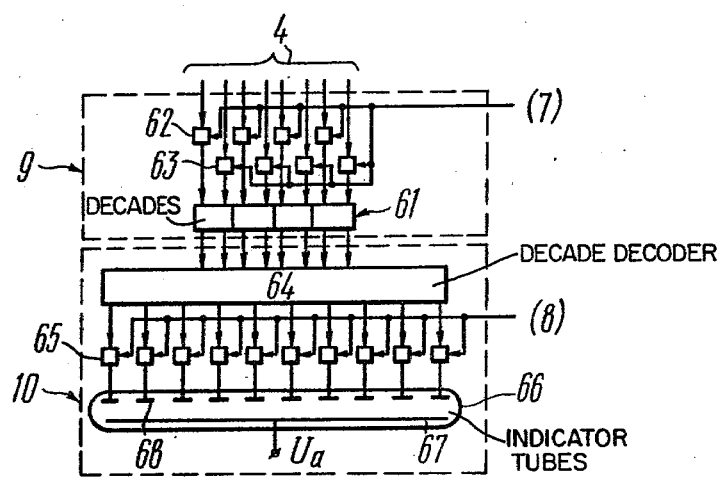
FIG. 4 is a functional diagram of a register according to the invention connected to a digital display unit.

FIG. 4 illustrates an alternative connection of the digital display unit 10 to the register 9. The digital display unit may be connected to the register 9 in other ways.

The register 9 comprises several decades 61, of the same type, and two groups of input gates 62 and 63.

The inputs of the gates 62 form the information input of the register whereto there are applied signals from the reset digit outputs of the respective decade of the reversible counter 4, whereas inputs of the gates 63 form the information input of the register, whereto there are applied signals from set digit outputs of the respective decade of the reversible counter 4. The outputs of the gates 62 are connected to the reset digit inputs of the decades 61, whereas outputs of the gates 63 are connected to set digit inputs of the decades 61. The control inputs of the gates 62 and 63 are combined and form the control input of the register 9.

The digital display unit 10 comprises a decade decoder 64, switches 65 and indicator tubes 66. Inputs of the decoder 64 form the information input of the digital display unit 10. Outputs of the decoder 64 are connected to inputs of the switches 65. Control inputs of the switches 65 are combined and serve as the control input of the digital display unit 10. An anode 67 of the indicator tube 66 is connected to a source of anode voltage $U_a$. Cathodes 68 of the indicator tube 66 comprise ten digits and are connected to the outputs of the switches 65.

Figure 5:
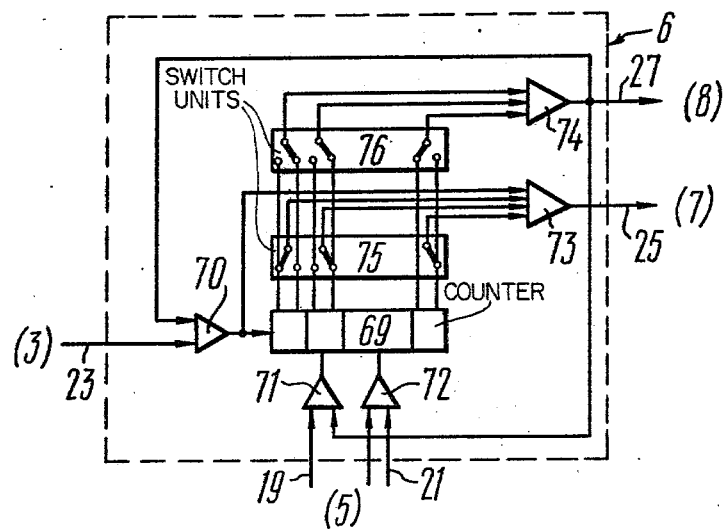
FIG. 5 is a preferred embodiment of a first time interval discriminator according to the invention.

FIG. 5 shows a preferred embodiment of the first time interval discriminator 6 constructed as a controlled time counter for selecting time intervals during which the predetermined temperature increments occur.

The discriminator includes a counter 69, three gates 70, 71, 72, two AND gates 73, 74, and two switch units 75, 76.

The inputs of the AND gates 74 are connected via the switch unit 76 to the digit outputs of the counter 69, the set and reset output of each digit of the counter 69 being connected of two poles of a respective switch of the switch unit 75, whereas the central taps of all the switches of the switch unit 76 are connected to the inputs of the AND gate 74. By changing the position of the switch of the switch unit 76, and inputs of the AND gate 74 can be connected to the set or reset output of the respective digit of the counter 69.

The output of the AND gate 74 is connected to the control inputs of the gates 70, 71, 72. This output is the information output of the controlled time counter and the output 27 of the discriminator 6.

The input of the gate 70 is the count of the controlled time counter, and the count input 23 of the discriminator 6. The output of the gate 70 is connected to the count input of the counter 69 and to the input of the AND gate 73. The other inputs of the AND gate 73 are connected through the switch unit 75 to the digit outputs of the counter 69. The output of the AND gate 73 is the intermediate output of the controlled time counter, and the intermediate output 25 of the discriminator 6. The inputs of the gates 71, 72 are the set inputs of the controlled time counter, and the reset inputs 19, 21 of the discriminator 6.

The outputs of the gates 71, 72 are connected to the reset inputs of the counter 69. By changing the position of the switches of the switch unit 75, the discriminator 6 is adjusted to the predetermined time interval $\tau_{01}$, whereas by changing the position of the switches of the switch unit 76, the discriminator 6 is adjusted to another predetermined time interval $\tau_{02}$. The position of the switches of the switch unit 76 must correspond to a binary number $\bar{n}_{02}$ derived from the relationship $$n_{02} = \tau_{02} \cdot f \quad (1)$$

where f is the frequency of synchronized clock pulses. For example, if the required threshold $\tau_{02}$ is equal to 5 seconds, at the frequency f=4 Hz the number $n_{02}$ equals 20 (binary number $n_{02} = 10100$). Consequently, the switches of the third and fifth digits of the switch unit 76 must be connected to the set outputs of the respective digits of the counter 69, whereas the reset of the switches must be connected to the reset outputs thereof.

The position of the switches of the switch unit 75 must correspond to a binary number $\bar{n}_{01}$ derived from the relationship $$n_{01} = \tau_{01} \cdot f - 1 \quad (2)$$

For example, if the required threshold $\tau_{01}$ is 0.75 seconds, at the frequency f=4 Hz the number $n_{01}$ equals 2 (binary number $n_{01} = 10$). Consequently, the switch of the second digit of the switch unit 75 must be connected to the set output of the counter 69, whereas the reset of the switches must be connected to the reset outputs thereof.

Figure 6:
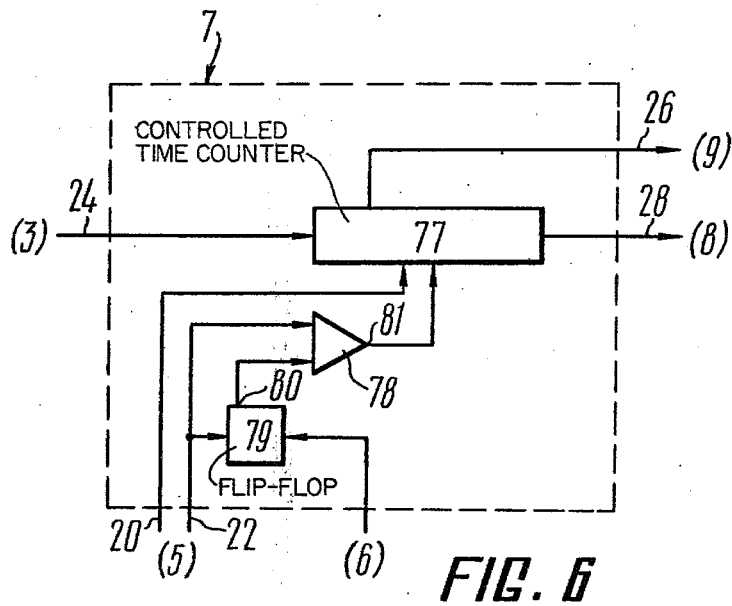
FIG. 6 is a preferred embodiment of a second time interval discriminator according to the invention.

FIG. 6 shows a preferred embodiment of the discriminator 7 of time intervals during which the predetermined temperature increment occurs within a period of time exceeding the predetermined value.

The discriminator 7 has a controlled time counter 77, a gate 78, and a flip-flop 79.

The construction of the controlled time counter 77 may be identical to that shown in FIG. 5. In such a case, however the controlled time counter is adjusted with the aid of the switch unit 76 to another predetermined time interval $\tau_{03}$, where $\tau_{03} > \tau_{02}$.

A count input of the time meter 77 is the count input 24 of the discriminator 7, whereas its intermediate output is the intermediate output 26 of the discriminator 7.

A first reset input of the time counter 77 is the first reset input 20 of the discriminator 7, whereas its information output is the output 28 of the discriminator 7. A reset input of the flip-flop 79 is a disable input of the discriminator 7. A set input of the flip-flop 79 combined with an input of the gate 78 is the second reset input 22 of the discriminator 7. An output 80 of the flip-flop is connected to a control input of the gate 78, and an output 81 of said flop-flop is connected to a second reset input of the controlled time counter 77.

The digital analyzer for determining the liquidus temperature operates as follows.

A signal carrying information of the actual temperature of the metal being analyzed in the process of cooling is applied to the input 11 (FIG. 1) of the converter 1. Depending on the sign of the signal increment, a train of code pulses is applied from the outputs 12 and 13 of the converter 1 through the synchronization unit 3 to the add and subtract inputs 15, 17 of the reversible counter 4. As a result, in the reversible counter 4 there is formed a parallel code of the actual temperature of the metal or alloy being analyzed.

From the outputs of the synchronization unit 3, the synchronized code pulses are also applied to the inputs 16 and 18 of the discriminator 5 of the local temperature increments. The synchronized clock pulses are applied to the count inputs 23 and 24 of the discriminators 6 and 7.

On the portion I of the cooling curve (FIG. 7) the time interval discriminators 6, 7 (FIG. 1) are reset each time by the pulses arriving at the inputs 19 and 20 of the discriminator 6 and 7 at the moment when the change of the signal applied to the input II of the converter 1 exceeds the value corresponding to the threshold $+\epsilon_0$ whereto the discriminator 5 is adjusted. In this case, at the intermediate outputs 25 and 26 of the discriminators 6 and 7 no pulses are formed because, due to a rapid change of the signal on this portion, the time intervals $t_2 - t_1$ (FIG. 7) between two successive moments of arrival of pulses from the first output of the discriminator 5 (FIG. 1), is less than the predetermined threshold $\tau_{01}$.

On the portion II of the cooling curve (FIG. 7) the pulses from the second output of the discriminator 5 (FIG. 1) continue to reset the discriminator 6. In so far as on the whole portion II of the cooling curve (FIG. 7), due to a rapid change of the actual temperature signal, the time intervals $t_4 - t_3$ between two successive moments of the arrival of pulses from the second output of the discriminator 5 (FIG. 1) still remain less than the threshold $\tau_{01}$, no pulses are formed at the intermediate output 25 of the discriminator 6. Therefore, on the portion II (FIG. 7) the resetting of the discriminator 7 (FIG. 1) is not blocked and the discriminator 7 will be reset each time by the pulses arriving from the second output of the discriminator 5.

At the moment when crystallization starts, the rate of cooling of the metal or alloy being analyzed sharply decreases, and at the temperature $T_l$ (FIG. 7) of the cooling curve there occurs a break.

In the process of crystallization of the metal or alloy on the portion III of the cooling curve, the time interval $t_6-t_5$ between the two successive moments of the arrival of pulses from the second output of the discriminator 5 (FIG. 1), becomes greater than the threshold $\tau_{01}$. As a result, at the moment $t_5+\tau_{01}$ (FIG. 7) there is formed a pulse at the intermediate outputs 25 and 26 (FIG. 1) of the discriminators 6 and 7. From the intermediate output 26, the pulse is applied to the control input of the register 9 due to which the temperature code of the metal being analyzed $T_l'$ (FIG. 7) is entered into the register 9. From the intermediate output 25 (FIG. 1) the pulse is applied to the disable input of the discriminator 7. In this case the resetting of the discriminator 7 is blocked.

At the moment $t_6$ (FIG. 7) when the local increment of temperature assumes the threshold $-\epsilon_0$, at the second output of the discriminator 5 (FIG. 1) there is formed another pulse which is applied to the inputs 21 and 22 of the discriminators 6 and 7. This pulse resets the discriminator 6.

As mentioned above, the discriminator 7 cannot be reset at the moment $t_6$ (FIG. 7) because at the preceding moment $t_5+\tau_{01}$ there was applied to its disable input a pulse from the intermediate output 25 (FIG. 1) of the discriminator 6. As will be clear from the rest of the disclosure, the discriminator 7 operates in a manner that the pulse arriving at its input 22 enables resetting of the discriminator 7.

In the process of crystallization of the metal or alloy on the whole portion of the cooling curve (FIG. 7), the pulses from the second output of the discriminator 5 (FIG. 1) reset the discriminator 6 each time when the local temperature change of the metal or alloy being analyzed assumes the threshold $-\epsilon_0$. After each successive resetting of the discriminator 6, when a time interval equal to $\tau_{01}$ elapses, there is formed a pulse at its intermediate output 25. Each such pulse arriving at the disable input of the discriminator 7 blocks the resetting of the discriminator 7. As a result, when a time interval equal to $\tau_{03}$ elapses, i.e. at the moment $t_7=t_5+\tau_{03}$ (FIG. 7) after resetting the discriminator 7 (FIG. 1), at the output 28 of the discriminator 7 there is formed a signal, as the duration of the anomalous sloping portion exceeds the threshold $\tau_{03}$. As soon as this signal occurs, it is clear that the anomalous sloping portion is caused by the thermal effect of phase transformation of the metal or alloy and, hence, the temperature $T_1$ of the metal or alloy at which there appears a break (FIG. 7) of the cooling curve is the liquidus temperature. The signal from the output 28 (FIG. 1) of the discriminator 7 is applied through the OR gate 8 to the control input of the digital display unit 10. At this moment the information contained in the register 9 is transmitted to the digital display unit 10 in the form of the temperature code $T_l'$ (FIG. 7) which differs from the liquidus temperature $T_l$ by a value not exceeding $\epsilon_0$.

Figure 7:
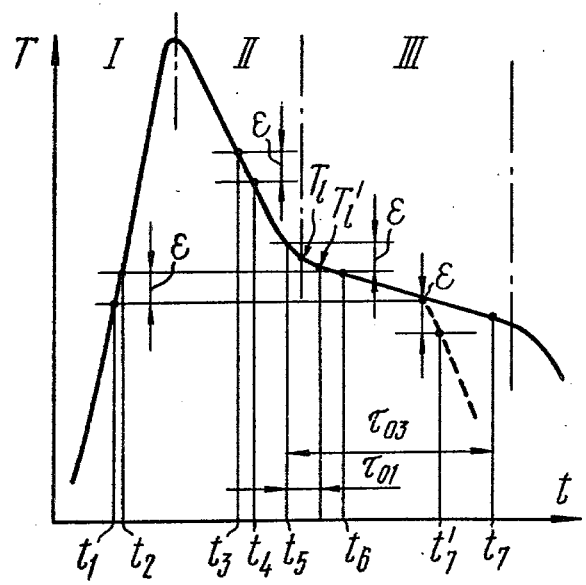
FIG. 7 is a cooling curve whereon an anomalous sloping portion occurs during crystallization.

In case the anomalous sloping portion is caused by the pseudothermic effect and its duration is less than the threshold $\tau_{03}$, then, as can be seen in FIG. 7, from the moment $t_7' < t_7$ when the time intervals between the two successive moments of the arrival of pulses from the second output of the discriminator 5 (FIG. 1) again become less than the threshold $\tau_{01}$, the discriminator 7 is reset. In this case at the output 28 of the discriminator 7 no signal appears during the whole period of the analysis. The absence of this signal rules out the possibility of transmitting false information on the analysis result to the digital display unit 10. As can be seen from the description of the operating principle of the analyzer, as soon as a break appears on the cooling curve, the code of metal or alloy temperature at which the break of the cooling curve occurs, is stored and the decision that the temperature is the liquidus temperature is taken only when the duration of the anomalous sloping portion exceeds the predetermined threshold $\tau_{03}$.

Figure 8:
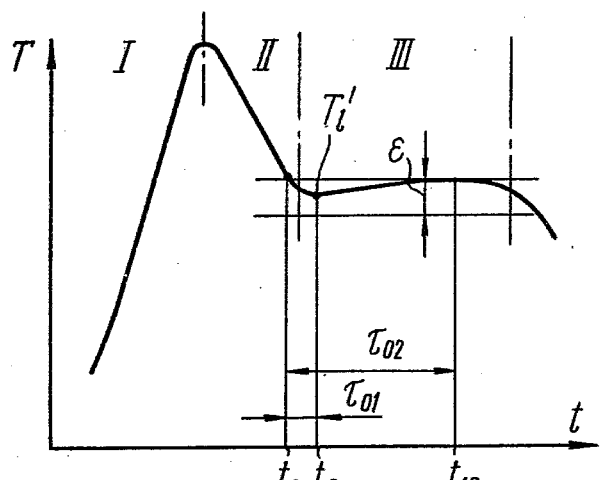
FIG. 8 is a cooling curve whereon an anomalous horizontal portion occurs during crystallization.

In case a horizontal anomalous portion (FIG. 8) occurs on the cooling curve, the analyzer processes the portions I and II of the cooling curve in the manner described above. On the portion III which occurs during crystallization of metal or an alloy, no pulses are formed at the outputs of the discriminator 5 (FIG. 1), because the local temperature increments of the metal or alloy do not exceed the threshold $\pm\epsilon_0$. In this case, beginning from the moment $t_8$ (FIG. 8), the discriminators 6 and 7 (FIG. 1) cease being reset. At the moment $t_9=t_8+\tau_{01}$ (FIG. 8) there is formed a pulse at the intermediate output 26 (FIG. 1) of the discriminator 7. This pulse is applied to the control input of the register 9. As a result, the temperature code $T_l'$ (FIG. 8) of the metal or alloy is entered in the register 9. As soon as the time equal to $\tau_{02}$ ($\tau_{02}<\tau_{03}$) elapses after the resetting of the discriminators 6 and 7 (FIG. 1), i.e. at the moment $t_{10}=t_8+\tau_{02}$ (FIG. 8) there is formed a signal at the output 27 (FIG. 1) of the discriminator 6. This signal, through the OR gate 8, is applied to the control input of the digital display unit 10. In this case, the latter is fed with information on the liquidus temperature of the metal or alloy being analyzed, delivered in the form of the temperature code $T_l'$ (FIG. 8) which may differ from the actual liquidus temperature $t_1$ by a value not exceeding $\epsilon_0$.

The operating principle of the converter 1 shown in FIG. 2 is illustrated by the time plots of FIGS. 9 and 10.

The slide contact 39 of the automatic potentiometer 40 moves parallel to the holder 38 of the converter 1, the luminous flux of the light source 37, incident on the photodiodes 35 and 36, being modulated by the marks 33 and 34 of the measuring scale 32. The signals from the photodiodes 35 and 36 are applied to the inputs of the Schmitt triggers 41 and 42, respectively.

As the slide contact 39 moves from left to right, the signal (FIG. 9a) of the photodiode 35 is a quarter of a period behind the signal (FIG. 9b) of the photodiode 36. In this case the signal (FIG. 9c) at the set output and the signal (FIG. 9c) at the reset output of the Schmitt trigger 41 are a quarter of a period behind the signal (FIG. 9e) at the set output and the signal (FIG. 9f) at the reset output of the Schmitt trigger 42, respectively.

The pulse shaper 43 forms pulses (FIG. 9g) on the positive edge of the signal (FIG. 9l) arriving from the set output of the Schmitt trigger 42. The pulse shaper 44 forms the pulses (FIG. 9h) on the positive edge of the signal (FIG. 9f) arriving from the reset output of the Schmitt trigger 42.

The pulses (FIG. 9g) from the output of the pulse shaper 43 are applied to the pulse input of the gate 45. The pulses (FIG. 9h) from the output of the pulse shaper 44 are applied to the pulse input of the gate 46. The signals (FIG. 9d) from the reset output of the Schmitt trigger 41 are applied to the control inputs of the gates 45 and 46. As can be seen from the time plot (FIG. 9), at the moments when the signals are applied to the pulse input of the gate 45 (FIG. 2), the gate 46 is blocked because there is applied to its control input a disable signal from the reset output of the Schmitt trigger 41. At the moments when the signals are applied to the pulse input of the gate 46, the gate 45 is conductive because to its control input there is applied an enable signal from the reset output of the Schmitt trigger 41.

Therefore, as the slide contact 39 (FIG. 2) moves from left to right, no signals (FIG. 9i) are formed at the output of the gate 45. The signals (FIG. 9j) at the output of the gate 46 are code pulses of the converter 1, corresponding to a positive increment of temperature on the cooling curve.

As the slide contact 39 moves from right to left the signal (FIG. 10a) of the photodiode 35 is a quarter of a period ahead of the signal (FIG. 10b) of the photodiode 36 a. Hence, at the moments when the pulses (FIG. 10g) of the pulse shaper 43 are applied to the pulse input of the gate 45 to the control input thereof there are applied enabling signals (FIG. 10d) from the reset output of the Schmitt trigger 41 (FIG. 2). At the moments when pulses (FIG. 10) of the pulse shaper 44 are applied to the disable pulse input of the gate 46 to the control input thereof there are applied disable signals (FIG. 10d) from the reset output of the Schmitt trigger 41.

Hence, when the slide contact 39 moves from right to left no signals (FIG. 10j) are formed at the output of the gate 46. The signals (FIG. 10i) at the output of the gate 45 (FIG. 2) are code pulses of the converter 1 corresponding to a negative increment of temperature on the cooling curve.

At the moments when the clock pulses (FIG. 11a) from the generator 2 are applied to the count input of the flip flop 50 (FIG. 3) of the unit 47 for distributing the clock pulses, the state of this flip flop successively changes. The signals from the set output (FIG. 11c) and reset output (FIG. 11b) of the flip-flop 50 are applied to the control inputs of the gates 51 and 52, respectively. To the pulse inputs of said gates there are applied clock pulses (FIG. 11a) from the generator 2. As a result, at the outputs of said gates there are formed two trains of pulses shifted in time relative to each other. In this case at the output of the gate 51 there are formed synchronized clock pulses (FIG. 11d) whereas at the output of the gate 52 there are formed synchronizing clock pulses (FIG. 11e).

The repetition frequency $f_1$ of the synchronized clock pulses is equal to the of repetition frequency $f_2$ of the synchronizing clock pulses and is $$f_1 = f_2 = \tfrac{1}{2} f_0, \qquad (3)$$

where $f_0$ is the repetition frequency of pulses arriving from the output of the clock pulse generator 2.

The synchronized clock pulses are applied to the respective third output of the synchronization unit 3.

The synchronizing clock pulses are applied to the inputs of the AND gate 57 and the gate 59 of the synchronization unit 48, and to the inputs of the AND gate 58 and the gate 60 of the synchronization unit 49. In the initial state, all the flip-flop 53, 54, 55, 56 are zeroed. As from the output of the converter 1 there is applied a code pulse (FIG. 11g) corresponding to a positive increment of temperature on the cooling curve, the flip-flop 53 is set (FIG. 11h). After a change in the state of the flip-flop 53 at the moment of the arrival of the next successive synchronizing clock pulse, at the output of the AND gate 57 there is formed a pulse (FIG. 11i). This pulse sets the buffer flip-flop 55 (FIG. 11k), thereby driving the gate 59 into conduction. At the moment of arrival of the next successive clock pulse (FIG. 11j) at the output of the gate 59 there is formed a synchronized code pulse (FIG. 11l) corresponding to a positive increment of temperature on the cooling curve. This pulse is applied to the respective output of the synchronization unit 3 and to the inputs of the flip-flop 53 and 55. The signal (FIG. 11j), arriving from the reset output of the flip-flop 55 at one of the inputs of the AND gate 57, precludes the arrival of the pulse at the unit input of the 55 at the moment when the pulse is applied to the reset input of the flip-flop 55. When formed, the synchronized code pulse zeroes the flip-flops 53 and 55, thereby preparing the synchronization unit 48 for receiving the next pulse.

In the coperation of the synchronization unit 48 there may be a case, when the code pulse partially coincides in time with the synchronizing clock pulse. This may bring about the occurrence of an invalid pulse (FIG. 11i) at the output of the AND gate 57, for example, a pulse having an insufficient duration or amplitude. When such an invalid pulse occurs, the buffer flip-flops 55 may continue to be zeroed until the next synchronizing clock pulse is applied to the input of the AND gate 57. In so far as at the moment when the next synchronizing clock pulse is fed, the state of the flip-flops 53 cannot change any longer, at the output of the AND gate 57 at said moment there is formed another valid pulse (FIG. 11i). This pulse sets the flip-flops 55. At the moment of the arrival of the next synchronizing clock pulse (FIG. 11e), at the output of the gate 59 there is formed a synchronized code pulse (FIG. 11) which is applied to the respective output of the synchronization unit 3, and simultaneously sets the flip-flops 53 and 55.

In the same manner, at the output of the gate 60 of the synchronization unit 49 there are formed synchronized code pulses corresponding to a negative increment of temperature on the cooling curve. These pulses are applied to the respective output of the synchronization unit 3.

Thus, a coincidence in time of the pulses formed at the outputs of the gates 59 and 60 with the pulses arriving from the output of the gate 52 of the unit 47 for distributing pulses, provides time separation of the synchronized clock pulses and the synchronized code pulses.

To ensure reliable operation of the synchronization unit 3, it is necessary that the repetition frequency $f_2$ of the synchronizing clock pulses be two or three times greater than the maximum repetition frequency $f_{3max}$ of the code pulses arriving from the outputs 12, 13 (FIG. 1) of the converter 1, i.e.

$$f_2 = 3 f_{3max} \qquad (4)$$

Hence, the pulse frequency at the output of the generator 2 must be equal to $$f_0 = 2 f_2 \geq 6 f_3 \qquad (5)$$

The operating principle of the discriminator 6 is as follows. After each resetting of the counter 69 (FIG. 5) by the pulses applied through the gates 71, 72 to any of its reset outputs, the counter 69 starts counting time by counting the synchronized clock pulses arriving through the gate 70 at the count input thereof. If in the counter there is formed a code $n_{01}$ corresponding to the threshold $\tau_{01}$ set with the aid of the switch unit 75, at the moment of the arrival of the next synchronized clock pulse, at the output of the AND gate 73 there is formed a pulse which is applied to the intermediate output 25 of the discriminator 6, and then, as soon as in the counter there is formed a code $n_{02}$ corresponding to the threshold $\tau_{02}$ set with the aid of the switch unit 76, at the output of the AND gate 74 there is formed a signal which is applied to the output 27 of the discriminator 6. Simultaneously, this signal blocks the gates 70, 71, 72 thereby blocking the counting and resetting of the counter 69, at the output of the discriminator 6 being retained till the next analysis cycle.

The operating principle of the time interval discriminator 7 is as follows. In the initial state, the flip-flop 79 is set and the enabling signal from its set output 80 renders the gate 78 conducting. If the pulses are not applied to the disable input of the discriminator 7, the flip-flop state remains unchanged and each pulse arriving at any of the reset inputs 20 or 22 of the discriminator 7, will set the counter 77. After each resetting of the counter 77, the latter starts a new time counting cycle by counting the synchronized clock pulses arriving at the count input of the counter 77.

If in this case, the time interval between the two successive arrivals of pulses fed to any of the inputs 20 or 22 of the discriminator 7, does not exceed the threshold $\tau_{01}$, no signals are formed at the intermediate output 26 and the output 28.

As soon as the signal is applied to the disable input of the discriminator 7, the flip-flop 79 is zeroed and the gate 78 is blocked. If at the next moment the pulse is applied to the input 22 of the discriminator 7, this pulse does not pass to the reset input of the counter 77 and the counter 77 continues counting the time interval. Simultaneously by the trailing edge of said pulse the flip-flop 79 is again set in its initial unity state. Thus, if in the process of the analysis, the moments of the arrival of pulses at the reset input 22 of the decoder 7 are preceded by the moments of the arrival of pulses at the disable input of the discriminator 7, the counter 77 continues the time counting started at the moment of its last resetting. If in the counter 77 there is formed a code corresponding to the predetermined threshold $\tau_{01}$, at the intermediate output 26 there is formed a pulse. In the same way, as soon as in the counter there is formed a code corresponding to the predetermined threshold $\tau_{03}$, at the information output of the counter there is formed a signal which is retained till the next successive analysis cycle.

At the moment of detecting a break on the cooling curve, there is formed a pulse, as shown above, at the intermediate output of the discriminator 7. This pulse is applied to the control input of the register 9. In this case, the input gates 62, 63 of the register 9 are opened, and the code from the reversible counter 4 in entered through the information input of the register 9 into the decades 61 thereof.

After checking the duration of the anomalous portion, from the output of the OR gate to the switches 65 of the digital display unit 10 there is applied a pulse, thereby closing the supply circuit of the indicator lamps 66. The indicator lamps are switched on and start digital display of the analysis results.

The device permits the anomalous sloping portion caused by the thermal effect of the phase transformation of metal or alloy to be distinguished with a sufficient degree of confidence from that caused by the pseudo-thermic effect.

The digital analyzer provides for a high accuracy of determining the liquidus temperature of metals and alloys when on the cooling curve there occurs an anomalous portion with a steep slope.

The employment of simplest functional computer units in the device ensures its high reliability, as well as a low cost and small dimensions.

Taken in combination with any known measuring devices for checking the carbon content in metal with reference to the liquidus temperature, the proposed device may perform the function of a digital sensor of carbon concentration in a closed control system for controlling steel melting processes with the use of a computer.

What is claimed is:

1. A digital analyzer for determining the liquidus temperature of metals and alloys, comprising
   a converter for converting the actual temperature of metals and alloys to a digital pulse code, having an input, whereto there is applied a signal carrying information on the actual temperature of a metal or alloy being analyzed in the process of cooling, a first output for code pulses corresponding to a positive increment of temperature, and a second output for code pulses corresponding to a negative increment of temperature;
   a clock pulse generator having an output;
   a synchronization unit for distributing clock and code pulses in time, having
      first, second and third inputs, a first output for synchronized code pulses corresponding to a positive increment of temperature, a second output for synchronized code pulses corresponding to a negative increment of temperature, and a third output for synchronized clock pulses;
   a reversible counter for generating a parallel code of the actual temperature, having an add input, a subtract input, and an information output;
   a discriminator of local temperature increments, having
      first and second inputs, a first output whereto a signal is applied with a predetermined positive increment of temperature, and a second output whereto a signal is applied with a predetermined negative increment of temperature;
   a first time interval discriminator for selecting time intervals during which the predetermined increment of temperature occurs, having
      a count input, a first reset input, a second reset input, an intermediate output and an output;
   a second time interval discriminator for selecting time intervals during which the predetermined increment of temperature occurs within a period of time exceeding said predetermined value, having
      a count input, a first reset input, a second reset input, a disable input for blocking said second reset input, an intermediate output, and an output;
   a register for storing the result of the analysis, having an information input, a control input, and an information output;
   an OR gate, having
      a first input, a second input and an output;
   a digital display unit for displaying the result of the analysis in a digital form, having
      an information input, and a control input;
   said first input of said synchronization unit, connected to said first output of said converter for converting the actual temperature of metals and alloys to a digital pulse code;

said second input of said synchronization unit, connected to said second output of said converter for converting the actual temperature of metals and alloys to a digital pulse code;

said third input of said synchronization unit, connected to said output of said clock pulse generator;

said first output of said synchronization unit, connected to said add input of said reversible counter and to said first input of said discriminator of local temperature increments;

said second output of said synchronization unit, connected to said subtract input of said reversible counter and to said second input of said discriminator of local temperature increments;

said third output of said synchronization unit, connected to said count input of said first time interval discriminator, and to said count input of said second time interval discriminator;

said first output of said discriminator of local temperature increments, connected to said first reset input of said first time interval discriminator and to said first reset input of said second time interval discriminator;

said second output of said discriminator of local temperature increments, connected to said second reset input of said first time interval discriminator and to said second reset input of said second time interval discriminator;

said intermediate output of said first time interval discriminator, connected to said disable input of said second time interval discriminator;

said output of said first time interval discriminator connected to said first input of said OR gate;

said output of said second time interval discriminator connected to said second input of said OR gate;

said intermediate output of said second time interval discriminator, connected to said control input of said register;

said information input of said register, connected to said information output of said reversible counter;

said information input of said digital display unit, connected to said information output of said register;

said output of said OR gate, connected to said control input of said digital display unit.

2. A digital analyzer as claimed in claim 1, wherein said second time interval discriminator comprises
a controlled time counter, having
a count input which is said count input of said second time interval discriminator, a first reset input which is said first reset input of said second time interval discriminator, a second reset input, an intermediate output which is said intermediate output of said second time interval discriminator, and an information output which is said output of said second time interval discriminator;
a gate for blocking said second reset output of said controlled time counter, having a control, input, an input and an output;
a flip-flop for controlling blocking of said second reset input of said controlled time counter, having
a reset input which is said disable input of said second time interval discriminator, a set input and a set output;
said set input of said flip-flop, combined with said input of said gate and serving as said second reset input of said second time interval discriminator;
said set output of said flip-flop, connected to said control input of said gate;
said output of said gate, connected to said second reset input of said controlled time counter.

* * * * *